(12) United States Patent
Peng (10) Patent No.: US 11,944,270 B1
(45) Date of Patent: *Apr. 2, 2024

(54) SYSTEMS AND METHODS OF ROTATION COMPENSATION FOR BRAIN OPTICAL IMAGING AND STIMULATION

(71) Applicant: PhotonEdge Inc., Pleasanton, CA (US)

(72) Inventor: Song Peng, Pleasanton, CA (US)

( * ) Notice: Subject to any disclaimer, the term of this patent is extended or adjusted under 35 U.S.C. 154(b) by 438 days.

This patent is subject to a terminal disclaimer.

(21) Appl. No.: 16/177,372

(22) Filed: Oct. 31, 2018

Related U.S. Application Data (60) Provisional application No. 62/588,898, filed on Nov. 20, 2017, provisional application No. 62/588,088, filed on Nov. 17, 2017.

(51) Int. Cl.
| | | |
|---|---|---|
| *A61B 1/00* | (2006.01) | |
| *A61B 1/04* | (2006.01) | |
| *A61B 1/07* | (2006.01) | |
| *A61B 1/313* | (2006.01) | |
| *A61B 90/20* | (2016.01) | |
| *G01D 5/347* | (2006.01) | |

(52) U.S. Cl.
CPC .......... *A61B 1/00126* (2013.01); *A61B 1/042* (2013.01); *A61B 1/043* (2013.01);
(Continued)

(58) Field of Classification Search
CPC ..... A61B 1/042; A61B 1/00126; A61B 90/20; A61B 1/313; A61B 1/043; A61B 1/07;
(Continued)

(56) References Cited

U.S. PATENT DOCUMENTS 6,471,637 B1 * 10/2002 Green ................ A61B 1/00045
600/137

2009/0142017 A1 * 6/2009 Merlet ................ G02B 6/3604
385/26
(Continued)

FOREIGN PATENT DOCUMENTS

| CN | 107049247 A | * | 8/2017 | |
| WO | WO-2011013011 A2 | * | 2/2011 | ......... A61B 1/00154 |
| WO | WO-2015109323 A2 | * | 7/2015 | ......... G02B 21/0064 |

OTHER PUBLICATIONS

Pierre M. Lane, Andrew L. P. Dlugan, Rebecca Richards-Kortum, and Calum E. MacAulay, "Fiber-optic confocal microscopy using a spatial light modulator," Opt. Lett. 25, 1780-1782 (2000) (Year: 2000).*

(Continued)

*Primary Examiner* — Aaron B Fairchild
(74) *Attorney, Agent, or Firm* — RADLO & SU; Peter Su (57) ABSTRACT

Embodiments of the present disclosure are directed to microendoscope instruments and methods that allows the imaging fiber to freely rotate with the animal while capturing images and projecting stimulation patterns with correct orientations. The microendoscope includes a first spatial light modulator for sourcing a first light source and generating a stimulated pattern to a fiber coupled to an imaging implant for attaching to the brain of the subject. A rotary joint is disposed between the microendoscope and the imaging implant to facilitate the movements and rotations of the imaging implant that is attached to the subject, thereby provides an essentially frictionless contact to brain of the subject so that the subject can freely moves and rotates without feeling the cumbersome imaging implant and fiber that are attached to the subject. A camera captures images obtained from the imaging implant with the specimen taken from the subject.

26 Claims, 7 Drawing Sheets

(52) U.S. Cl.
CPC ............... *A61B 1/07* (2013.01); *A61B 1/313* (2013.01); *A61B 90/20* (2016.02); *G01D 5/3473* (2013.01)

(58) Field of Classification Search
CPC ... A61B 5/0042; A61B 5/4064; A61B 5/6868; A61B 1/00183; A61B 90/361; A61B 1/00179; G01D 5/3473; G01D 5/34115; A61N 1/0529; G02B 21/0048; G02B 6/3604
USPC .................................................. 600/407, 137
See application file for complete search history.

(56) References Cited

U.S. PATENT DOCUMENTS

| | | | |
|---|---|---|---|
| 2010/0027025 A1* | 2/2010 | Nakabayashi | G01B 9/0205 356/482 |
| 2011/0098530 A1* | 4/2011 | Yamane | A61B 1/00172 600/109 |
| 2011/0137126 A1* | 6/2011 | French | A61B 5/0068 600/178 |
| 2015/0054445 A1* | 2/2015 | Kawai | A61B 1/0016 318/630 |
| 2015/0057549 A1* | 2/2015 | Flusberg | A61B 5/4064 600/476 |
| 2017/0176689 A1* | 6/2017 | Popp | G02B 6/3604 |
| 2018/0110581 A1* | 4/2018 | Kamata | A61B 90/25 |
| 2018/0296074 A1* | 10/2018 | Trulson | A61B 1/00179 |

OTHER PUBLICATIONS

Pierre M. Lane, Andrew L. P. Dlugan, Rebecca Richards-Kortum, and Calum E. MacAulay, "Fiber-optic confocal microscopy using a spatial light modulator," Opt. Lett. 25, 1780-1782 (Year: 2000).*

* cited by examiner

SYSTEMS AND METHODS OF ROTATION COMPENSATION FOR BRAIN OPTICAL IMAGING AND STIMULATION

CROSS REFERENCE TO RELATED APPLICATIONS

The present application claims priority to and the benefit of U.S. Provisional Application Ser. No. 62/588,088 entitled "Rotation Compensation for Brain Imaging and Stimulation," filed on 17 Nov. 2017, and U.S. Provisional Application Ser. No. 62/588,898 entitled "Multi-implant Patterned Stimulation," filed on 20 Nov. 2017, the disclosures of which are incorporated by reference herein in their entireties.

BACKGROUND

Technical Field

The present disclosure relates to fields of neuroimaging (or brain imaging technologies) and stimulation, and more particularly to microendoscope with optical fiber for brain fluorescence imaging.

Background Art

Neuroscience is a science discipline gaining an enormous amount of interests from researchers and scientists to enhance human understanding of physical, psychological and neurological conditions of brains for medical treatment and development of artificial intelligence. Microendoscope optical brain imaging provides a tool for the study and unraveling of mystery of neuroscience of animals. Optical fiber microendoscope is designed to image neural activity of animals as minimally invasive or non-invasive solutions.

One conventional solution provides a microendoscope to observe, research and study a free-moving animal with an imaging fiber typically fixed on the head of an animal. As the animal moves in a geographical area, the imaging fiber of the microendoscope gets twisted as the animal turns and rotates in different directions. The resulting torque from the twisting of the imaging fiber from the animal's head potentially could cause the imaging fiber to break. Even if the imaging fiber does not break, the resulting torque on the fixed imaging fiber on the animal's head may be too burdensome that the animal may be constrained from natural movements and instead turn back to comply with the forces as exerted from the torque on the animal, which in effect unnaturally affecting the animal's natural movements and behavior.

Accordingly, it is desirable to design a microendoscope with functional capabilities that would allow an animal to move freely while capturing optical images without impacting or constrain the natural motions of the animal.

SUMMARY OF THE INVENTION

Embodiments of the present disclosure are directed to instruments and methods that allows the imaging fiber to freely rotate with the animal while capturing images and projecting stimulation patterns with correct orientations. In a first embodiment, the microendoscope includes a first spatial light modulator for sourcing a first light source and generating a stimulation pattern to a fiber coupled to an imaging implant for attaching to the brain of the subject. A rotary joint is disposed between the spatial light modulator and the imaging implant to facilitate the movements and rotations of the imaging implant that is attached to the subject, thereby providing an essentially frictionless contact to brain of the subject so that the subject can freely move and rotate without feeling the cumbersome imaging implant and fiber that are attached to the subject. A camera captures images obtained from the imaging implant with the specimen taken from the subject, where the captured images may have rotated by certain angles due to the movements of the subject. A computer with an imaging computing software is coupled to the microendoscope for computing the degree of angular adjustments that are necessary to capture images from the camera in order to correctly placed the captured images with the correct image orientations and compensate for the positional shifts of the subject.

In a second embodiment, a rotation encoder is added to complement the rotary joint in the microendoscope to improve the accuracy in reading of the rotation angles from the captured images by the imaging implant, as well as reducing the amount of delay. The rotation encoder provides the reading of the angular information from any captured images that have been rotated so that the computer can more efficiently realign the images and the spatial light modulator can further rotate stimulation patterns.

In a third embodiment, the microendoscope possesses the capability to rotate images as a standalone instrument by including a rotation compensator that serves to rotate one or more optical images from the tip of the imaging implant. The selection of the rotation compensator is to complement the rotary joint such that the engineering relationship between the rotation compensator and the rotary joint depends on a particular choice of the rotation compensator relative to the rotary joint. In one implementation using a Dove prism, the rotation compensator rotates at half the speed of the rotary joint. To phrase it in another way, the rotary joint rotates at twice the speed of the rotation compensator. In one embodiment, the rotation compensator is set up to rotate in the same direction as the rotary joint. One of skilled in the art would recognize that other variations and engineering relationships between the rotation compensator and the rotation joint can be practiced without departing from the spirits of the present invention. The rotation compensator generates an output image that remains stationary even if the subject is active in motion. The spatial light modulator generates stimulation pattern that also remain stationary on specimen.

In a fourth embodiment, the combination of a rotary joint, a rotation compensator, and a rotation encoder in the microendoscope provides the ability of the encoder and the rotary joint to directly feed a rotation angle to a motor to rotate the rotation compensator, thereby eliminating any mechanical connection between the rotary joint and the rotation compensator. Absence of the rotation encoder, other embodiments described above to obtain a rotated angle from an optical image can be used to control the rotation compensator for compensating the orientation of the rotated optical image.

Broadly stated, an apparatus, comprises an instrument including a camera and a rotary joint; an imaging fiber having an instrument end coupled to the instrument and a distal end; and an imaging implant, coupled to the imaging fiber, inserted into a subject, the rotary joint rotating along with the motion of the subject through the imaging implant and the imaging fiber.

The structures and methods of the present disclosure are disclosed in detail in the description below. This summary does not purport to define the disclosure. The disclosure is defined by the claims. These and other embodiments, features, aspects, and advantages of the disclosure will become better understood with regard to the following description, appended claims, and accompanying drawings.

Additional features and advantages of embodiments will be set forth in the description, which follows, and in part will be apparent from the description. The objectives and other advantages of the invention will be realized and attained by the structure particularly pointed out in the example embodiments in the written description and claims hereof as well as the appended drawings. It is to be understood that both the foregoing general description and the following detailed description are illustrative and explanatory and are intended to provide further explanation of the invention as claimed.

BRIEF DESCRIPTION OF THE DRAWINGS

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying drawings. One or more embodiments are now described, by way of example only, with reference to the accompanying drawings wherein like reference numerals represent like elements and in which:

DETAILED DESCRIPTION

A description of structural embodiments and methods of the present invention is provided with reference to FIGS. 1-7. It is to be understood that there is no intention to limit the invention to the specifically disclosed embodiments but that the invention may be operated using other features, elements, methods, and embodiments that are known to those of skill in the art. Like elements in various embodiments are commonly referred to with like reference numerals.

Different arrangements described herein are provided by way of example only, and other arrangements and elements can be added or used instead and some elements may be omitted altogether. Also, those skilled in the art will appreciate that many of the elements described herein are functional entities that may be implemented as discrete components or in conjunction with other components, in any suitable combination and location, and various functions could be carried out by software, firmware and/or hardware.

Figure 1:
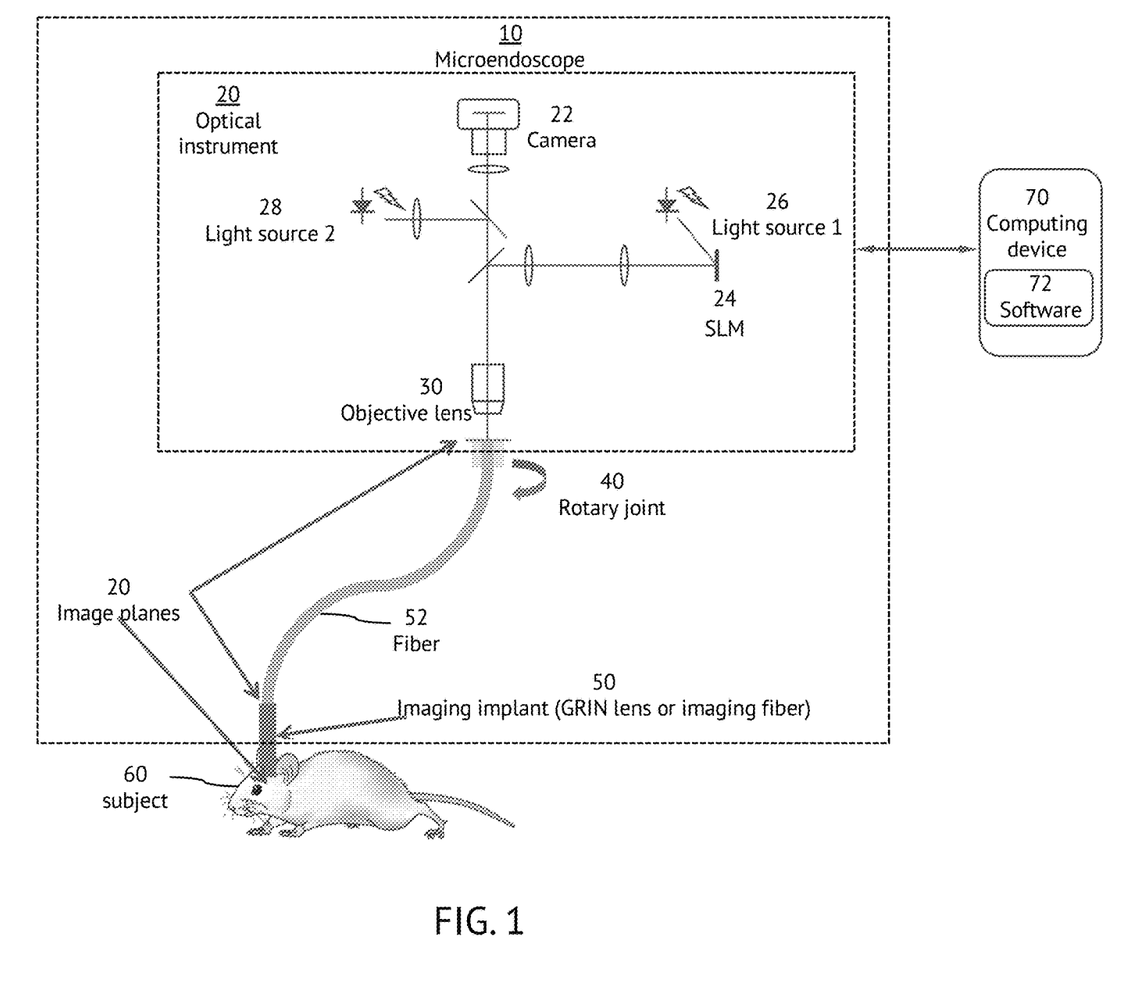
FIG. 1 is a system diagram illustrating a first embodiment of microendoscope with a rotary joint in accordance with the present invention.

FIG. 1 is a system diagram illustrating a first embodiment of microendoscope 10 comprising an optical instrument 20, a rotary joint 40 and an imaging implant 50 coupled to a subject 60. The optical instrument 20 includes a camera 22, a spatial light modulator (SLM) 24, a first light source 26, a second light source 28, and an objective lens 30. The rotary joint 40 is disposed between the optical instrument 20 and the imaging implant 50. The rotary joint 40 allows the subject 60 to be able to move freely because a fiber 52 and the imaging implant 50 rotate along the direction and movements of the subject 60. The rotary joint 40, for example, has ball bearings with low-friction, which enables the rotary joint 40 to rotate freely with the subject 50, without affecting the subject's 60 behavior or the rotational direction of the subject 60.

The camera 22 detects and analyzes certain fixed feature of the images or specimen from the subject generated from the tip of the imaging fiber 50. Images inside the camera 22 are also rotating as the rotary joint 40 and the fiber implant 50 move with the subject 60. A computing device 70 is coupled to the optical instrument 20 to extract rotation angles from the position of fixed feature or an image of the specimen of the subject 60 from the camera 22. The computing device 70 includes an imaging software 72 for adjusting and realigning each affected image based with the rotation angles. With the computation on the rotation angles, the spatial light modulator 24 in the microendoscope 10 is able to rotate the stimulation patterns by the specified rotation angles to offset the rotational directions and movements of the subject 60. The microendoscope 10 in the first embodiment comprises a system solution without the need of a rotation compensator by a combination of the rotary joint 40 that follows the natural movements of the imaging implant 50 attached to the subject 60, which then the camera 10 receives rotated images from the tip of the imaging implant 50 that the imaging software 72 calculates the amount of rotated angles, followed by the spatial light modulator 24 correspondingly adjusting the projected stimulation pattern by the specified rotated angled on to the brain of the subject 60.

As an example, initially, the spatial light modulator 24 projects a stimulation pattern onto the brain of the subject 60. The imaging implant 50 projects the light pattern to different spots on the brain of the subject 60 depending on the movement of the subject 60. In this example, the imaging implant 50 obtained three neuron cells from the brain of the subject 60. The camera 22 captures the images of three neuron cells in which the images reflect the one or more movements by the subject 60. The imaging software 72 computes to determine that the images have been rotated by 30 degrees from the movements of the subject 60, and therefore the imaging software 72 corrects the images by rotating 30 degrees to reflect the correct orientations of the images. The imaging software 72 also rotates the stimulation patterns on the spatial light modulator 24 by 30 degrees so that the stimulation patterns are projected to the same positions on subject 60.

The imaging implant 50 can be implemented, for example, with a gradient index (GRIN) lens or an imaging fiber. Alternatively, the rotary joint 40 can also be placed between a gradient index (GRIN) lens implant and the imaging fiber. The subject in instance is an animal, such as a mouse.

The imaging implant 50 in this embodiment is shown with a single imaging fiber, though a bundle of multiple imaging fibers can be implemented with the present invention. For a bundle of multiple imaging fibers, the common ends of the bundle would be coupled to the rotary joint 40, while the distal ends are used to image and stimulate different regions of the subject 60.

Figure 2:
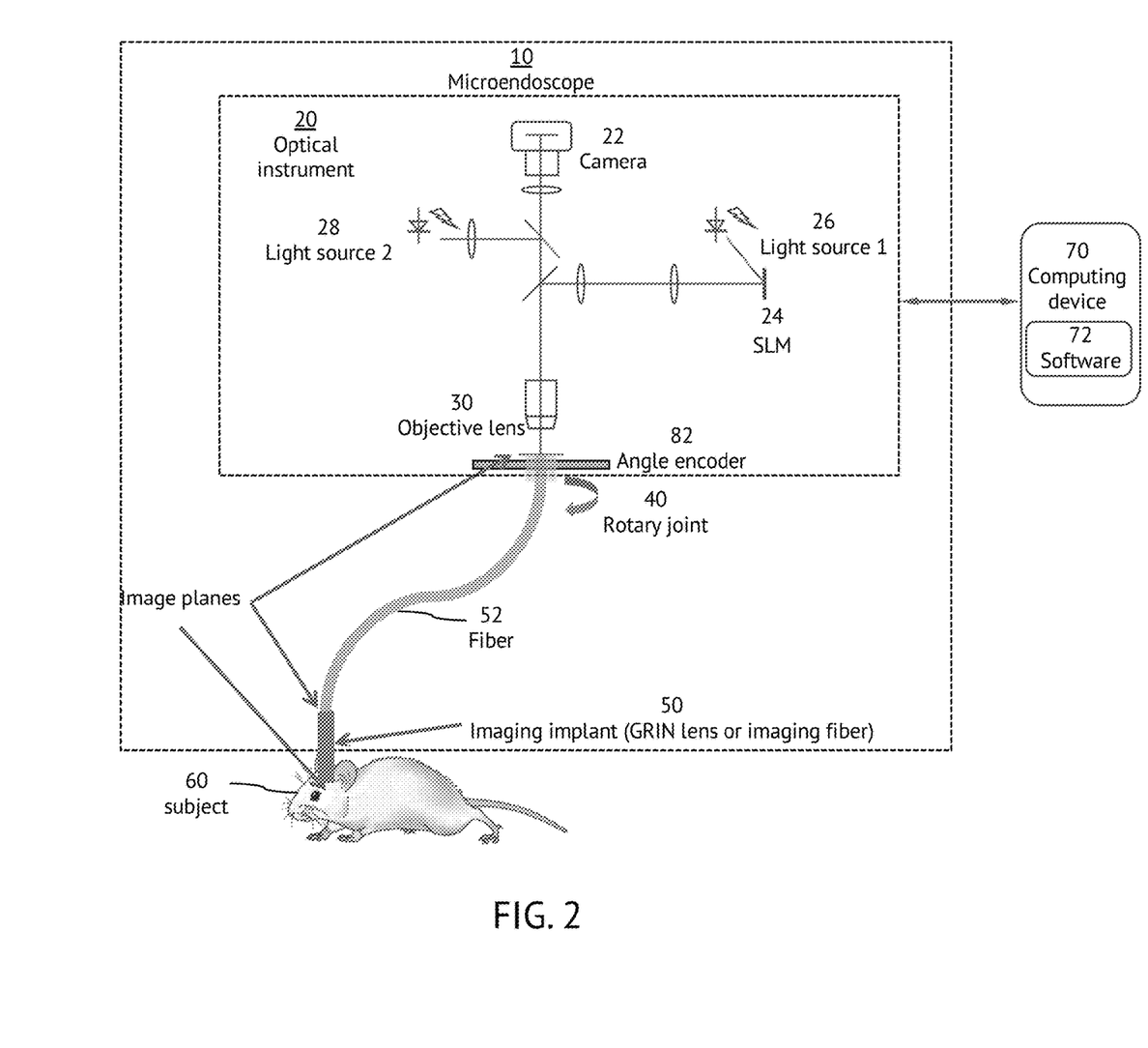
FIG. 2 is a system diagram illustrating a second embodiment of microendoscope with a rotary joint and an angle encoder in accordance with the present invention.

FIG. 2 is a system diagram illustrating a second embodiment of microendoscope 10 with a rotary joint 40 and an angle encoder 82 (also referred to as a rotation encoder). The microendoscope 10 includes the angle encoder 82, which is coupled to the rotary joint 40, for a more accurate read out of the rotation angles with a shorter delay. The angle encoder 82 produces angular information of the images captured by the imaging plant 50 to the computing device 70 for realigning the images, as well as for the spatial light modulator 24 to rotate the stimulation patterns.

Figure 3:
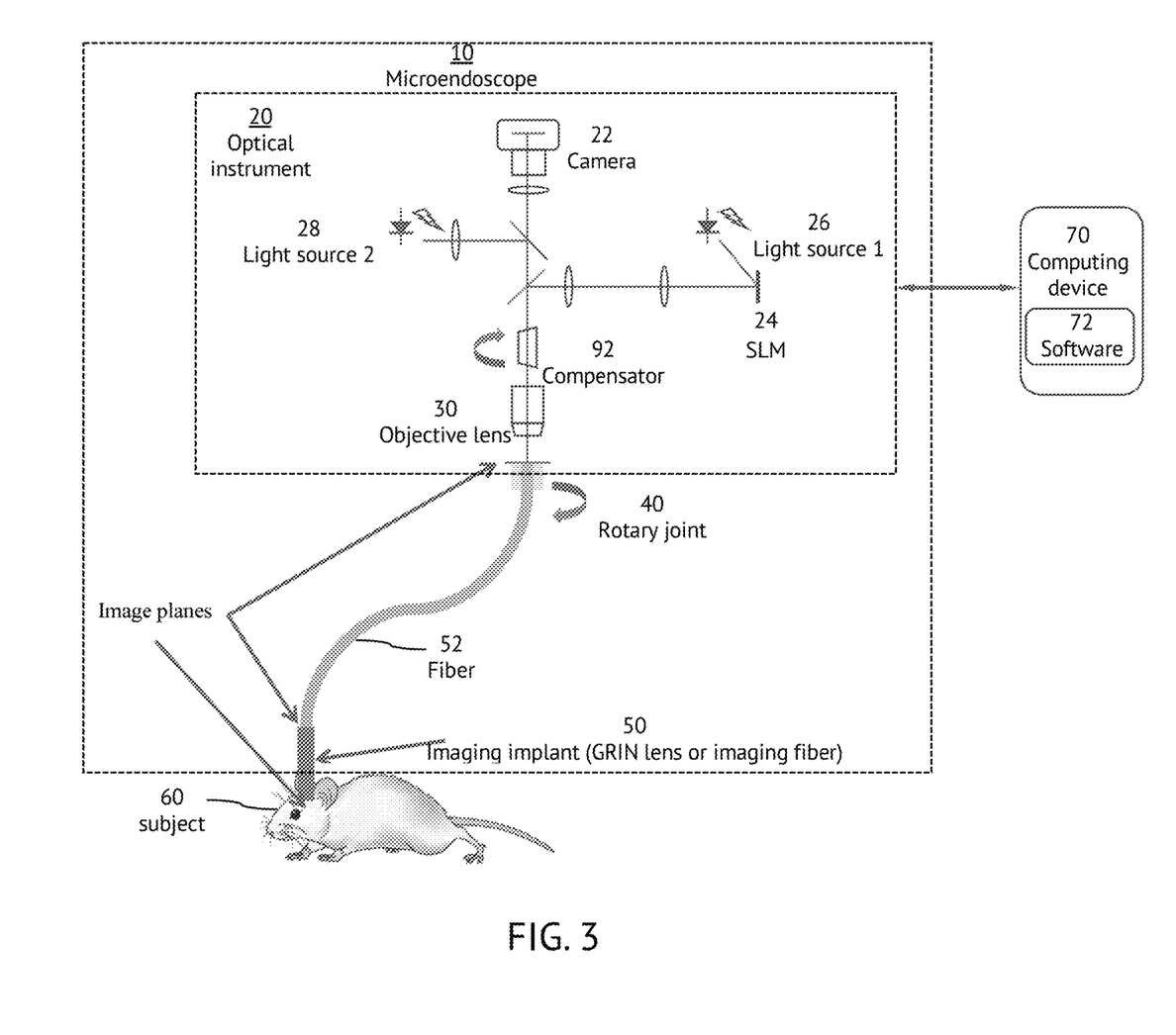
FIG. 3 is a system diagram illustrating a third embodiment of microendoscope with a rotary joint and a rotation compensator in accordance with the present invention.

FIG. 3 is a system diagram illustrating a third embodiment of the microendoscope 10 with the rotary joint 40 and a rotation compensator 92. The rotation compensator 92 serves to rotate back an optical image received from the imaging implant 50 of the subject 60. One suitable implementation of the rotation compensator 92 is a Dove prism. The correlation between an optical image and the Dove prism is that the output image rotates at twice the rotation speed of the Dove prism. One way to achieve this rotation ratio employs mechanical mechanisms to link the rotary joint 40 and the rotation compensator 92 which yield the rotation compensator 92 rotates at the half the speed relative to the rotational speed of the rotary joint 40. Preferably, in the example of implementing with a Dove prism, the rotation compensator 92 would rotate in the same direction as the direction of the rotary joint 40. The output image from the rotation compensator 92 remains stationary even as the subject 60 moves around. The stimulation patter from the spatial light modulator 24 also stays stationary on the specimen.

Optionally, an electrical motor can be added to enhance power assistance to the rotation compensator 92, particularly in embodiments where a chosen prism may be on the heavy side, as to hinder the movements of the subject or the weight of the rotation compensator 92 potentially could cause the fiber 52 to break. The addition of the electrical motor would assist the fiber to withstand the weight of the prism without breaking the fiber.

Figure 4:
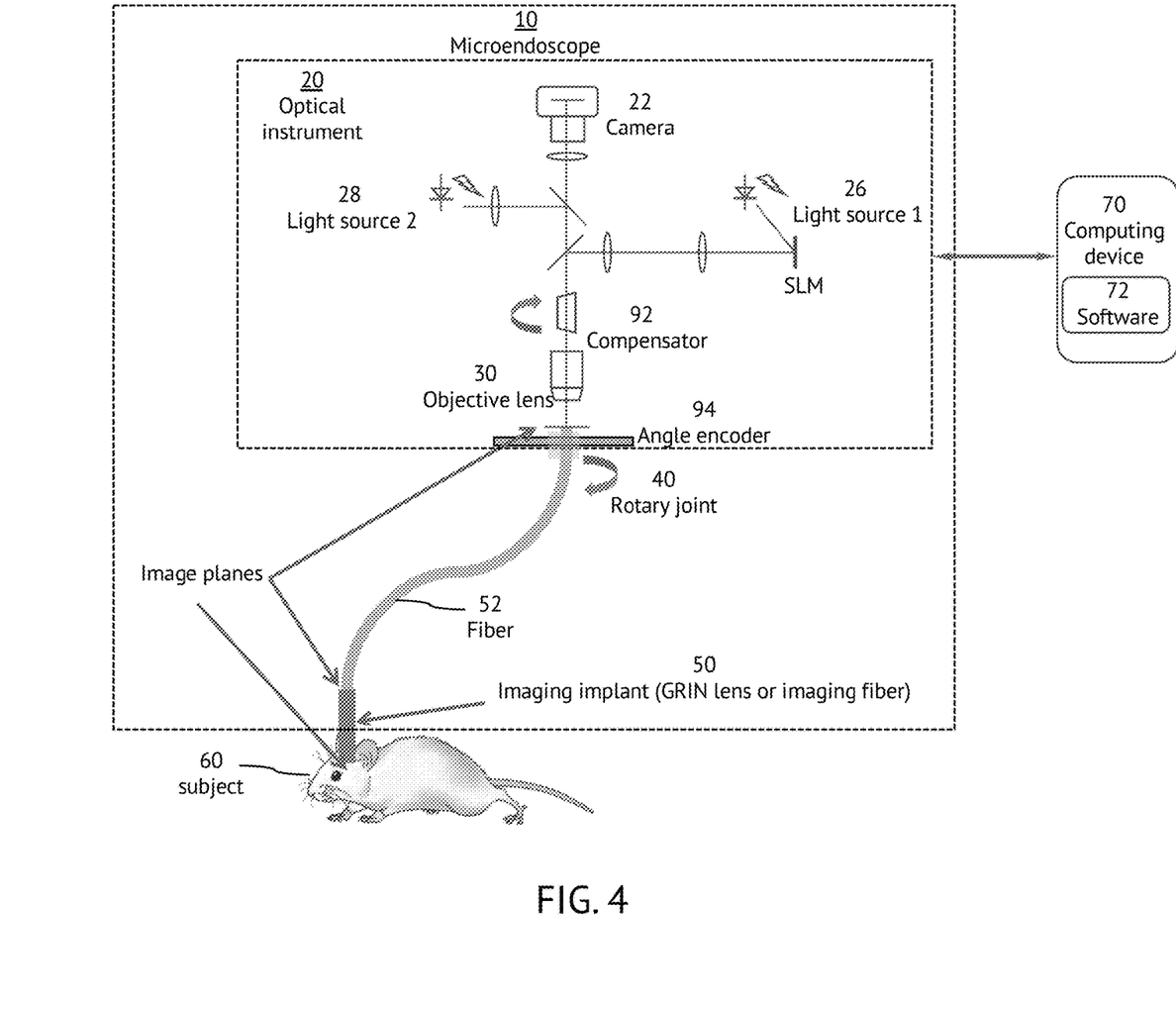
FIG. 4 is a system diagram illustrating a fourth embodiment of microendoscope with a rotary joint, a rotation compensator and an angle encoder in accordance with the present invention.

FIG. 4 is a system diagram illustrating a fourth embodiment of the microendoscope 10 with the rotary joint 40, the rotation compensator 92 and an angle encoder 94. The combination of the encoder 94 and the rotary joint 40 is able to directly feed a rotation angle to a motor to rotate the rotation compensator, thereby eliminates any mechanical connection between the rotary joint and the rotation compensator. Alternatively, without a rotation encoder, other embodiments described above to obtain a rotated angle from an optical image can be used to control the rotation compensator for compensating the orientation of the rotated optical image.

Figure 5:
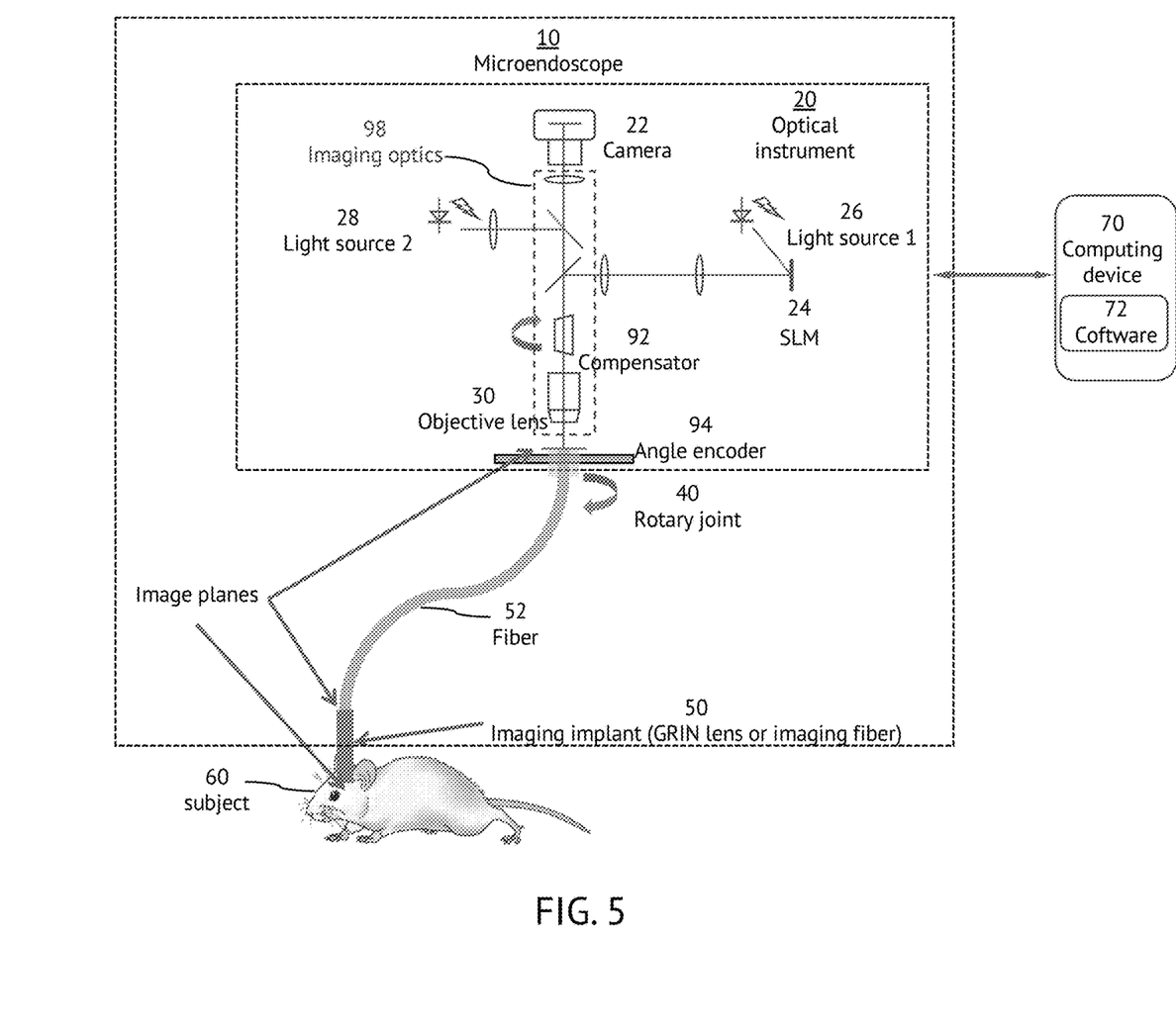
FIG. 5 is a system diagram illustrating the fourth embodiment of microendoscope with imaging optics, the rotary joint and the angle encoder in accordance with the present invention.
Figure 6:
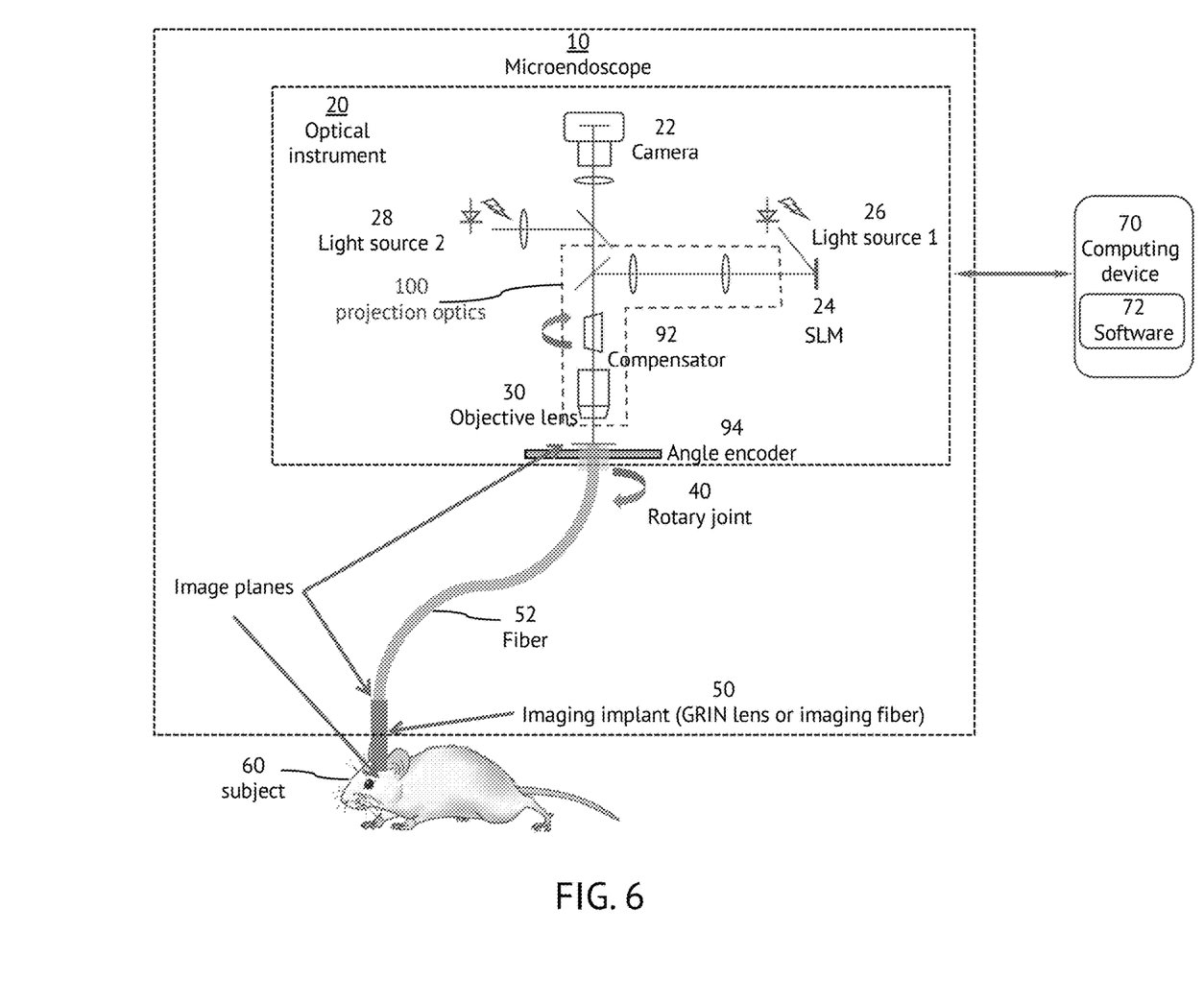
FIG. 6 is a system diagram illustrating the fourth embodiment of microendoscope with projection optics, the rotary joint and the angle encoder in accordance with the present invention.

In one alternative, FIG. 5 is a system diagram illustrating the fourth embodiment of microendoscope with imaging optics 98, the rotary joint and the angle encoder 94. The light source 28 provides illumination for the imaging optics 98. The imaging optics 98 shows one example of the imaging path from the camera 22. In this embodiment, the imaging optics 98 represent several optical components, including the objective lens, the rotation compensator 92 and optical lens. In another alternative, FIG. 6 is a system diagram illustrating the fourth embodiment of microendoscope with projection optics 100, the rotary joint 40 and the angle encoder 94. The projection optics 100 illustrates one example of the light path projected from the spatial light modulator 24. The projection optics 100 in this embodiment includes the objective lens 30, the rotation compensator 92, and other optical components.

Another embodiment provides a video camera system for monitoring and detecting the movements of an animal, which the data monitored or detected are fed back to correspondingly adjust the rotating platform of a microendoscope. One advantage of the video camera solution is that the optical system of the microendoscope would typically require no further modifications to track the brain imaging of an animal.

Figure 7:
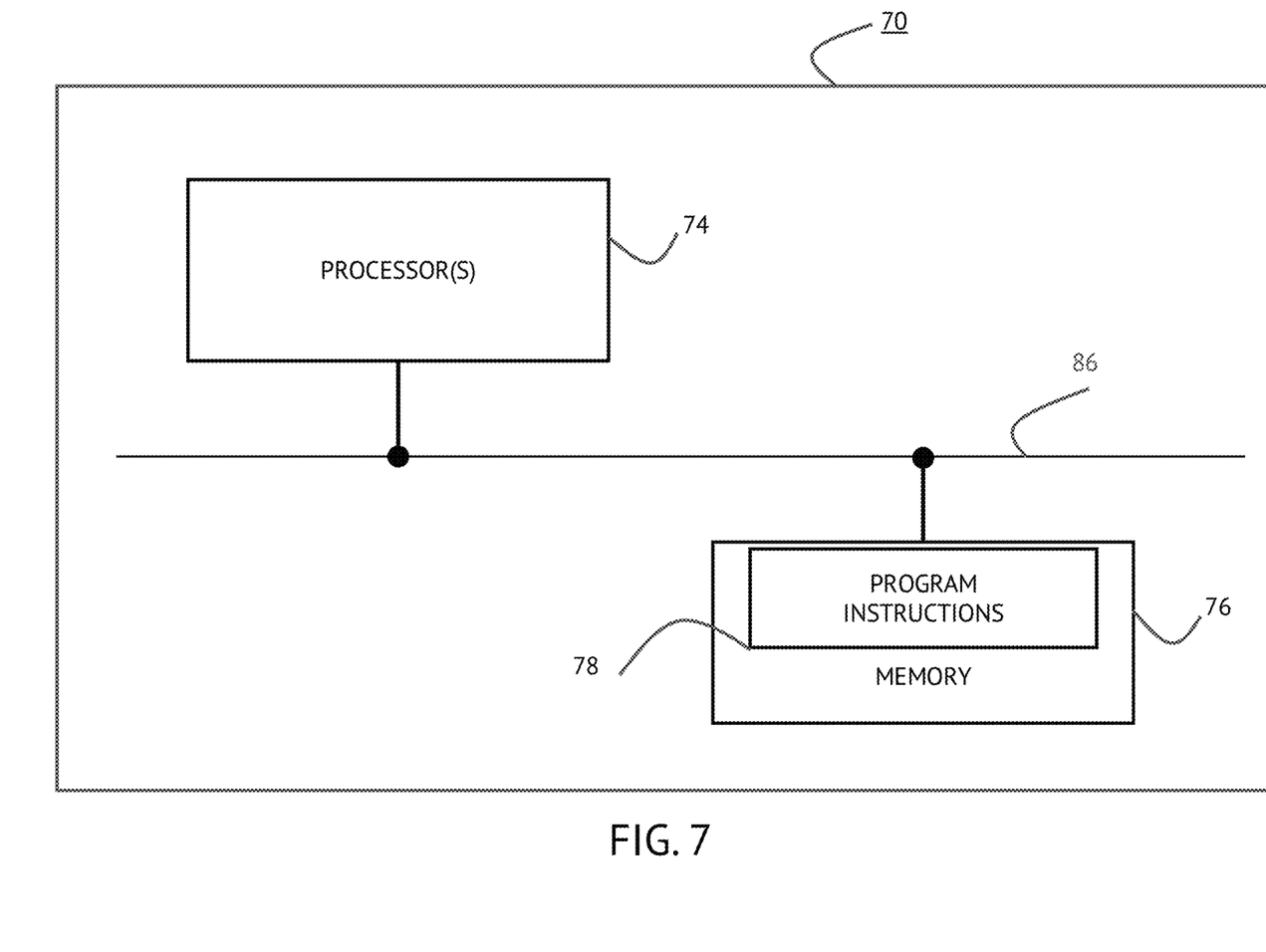
FIG. 7 is a simplified diagram of a computer processing system in accordance with the present invention.

Various functions described herein, such as in FIGS. 1-6 above, could be carried out by a processing system 70, as shown in FIG. 7. The system 70 includes at least one processor 74 and memory 76, coupled together via a bus 86. The processing system 70 may be, for example, incorporated in a separate controller controlling the element(s) of the microendoscope 10 (e.g., the spatial light modulato 24) or its components may be distributed fully or partially across the element(s) of the microendoscope 10. Various examples are possible.

In one embodiment, the processor(s) 74 may be dedicated processor(s) or general purpose processor(s) configured to execute computer-readable program code. The memory 76 may be volatile or non-volatile non-transitory computer-readable medium or media, now known or later developed. The memory 76 may hold program logic comprising program instructions 78 (e.g., machine language instructions) executable by the processor(s) 74 to carry out various functions described herein. Additionally, the memory 76 may store any other data, such as data used by the processor (s) 74 in the execution of the program instructions 78. However, any additional data may also be held in other data storage location(s) separate from the memory 76.

Further, although not shown in FIG. 7, the processing system 70 may include a number of interfaces, such as user interface(s), communication interface(s) (e.g., an interface for communicating data to/from the memory 76, etc.), and/or the like. Also, other elements (e.g., modules, input lines, buses, etc.) may be included as well.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B are satisfied by any one of the following: A is true (or present) and B is false (or not present), A is false (or not present) and B is true (or present), and both A and B are true (or present).

The terms "a" or "an," as used herein, are defined as one or more than one. The term "plurality," as used herein, is defined as two or more than two. The term "another," as used herein, is defined as at least a second or more.

The invention can be implemented in numerous ways, including as a process, an apparatus, and a system. In this specification, these implementations, or any other form that the invention may take, may be referred to as techniques. In general, the order of the connections of disclosed apparatus may be altered within the scope of the invention.

The present invention has been described in particular detail with respect to some possible embodiments. Those skilled in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component. An ordinary artisan should require no additional explanation in developing the methods and systems described herein but may nevertheless find some possibly helpful guidance in the preparation of these methods and systems by examining standard reference works in the relevant art.

These and other changes can be made to the invention in light of the above detailed description. In general, in the following claims, the terms used should not be construed to limit the invention to the specific embodiments disclosed in the specification and the claims, but should be construed to include all methods and systems that operate under the claims set forth herein below. Accordingly, the invention is not limited by the invention, but instead its scope is to be determined entirely by the following claims.

What is claimed and desired to be secured by Letters Patent of the United States is:

1. An apparatus, comprising:
   an instrument including a camera (22) and a rotary joint (40);
   an imaging fiber (52) having an instrument end and a distal end, the instrument end coupled to the instrument;
   an imaging implant (50), coupled to the imaging fiber, configured for mounting onto an animal subject;
   a rotary joint rotating (40) along with a motion of the animal subject through the imaging implant and the imaging fiber; and
   an angle encoder (94), coupled to the rotary joint, for reading out the rotating angle of the instrument end of the imaging fiber as the animal subject moves.

2. The apparatus of claim 1, wherein the instrument comprises one or more imaging optics for imaging the instrument end of the fiber onto the camera.

3. The apparatus of claim 1, wherein the instrument comprises a spatial light modulator (SLM).

4. The apparatus of claim 3, wherein the instrument comprises one or more projection optics for imaging the spatial light modulator onto the instrument end of the fiber.

5. The apparatus of claim 1, wherein the instrument comprises one or more light sources for illuminating the animal subject.

6. The apparatus of claim 1, wherein the instrument comprises one or more light sources for stimulating the animal subject.

7. The apparatus of claim 1, wherein the imaging implant comprises a gradient index (GRIN) lens.

8. The apparatus of claim 1, wherein the imaging implant comprises an imaging fiber.

9. The apparatus of claim 1, wherein the instrument comprises a rotation compensator disposed in an optical path for compensating the image rotation caused by the movement of the animal subject.

10. The apparatus of claim 9, wherein the rotation compensator comprises a Dove prism for rotating at half of the speed of the rotary joint.

11. The apparatus of claim 1, wherein the instrument comprises:
    a rotation compensator disposed in an optical path for compensating the image rotation caused by the movement of the animal subject; and
    a controller for reading the angle information from the angle encoder and controlling the rotation compensation based on the received angle information.

12. The apparatus of claim 11, wherein the rotation compensator comprises a Dove prism for rotating at half of the speed of the rotary joint.

13. The apparatus of claim 1, wherein the apparatus comprises a microendoscope.

14. An apparatus, comprising:
    an instrument including a camera (22) and a rotary joint (40);
    an imaging fiber (52) having an instrument end and a distal end, the instrument end coupled to the instrument;
    an imaging implant (50), coupled to the imaging fiber, configured for insertion into an animal subject, the rotary joint rotating (40) along with a motion of the animal subject through the imaging implant and the imaging fiber; and
    an angle encoder (94), coupled to the rotary joint, for reading out the rotating angle of the instrument end of the imaging fiber as the animal subject moves.

15. The apparatus of claim 14, wherein the instrument comprises one or more imaging optics for imaging the instrument end of the fiber onto the camera.

16. The apparatus of claim 14, wherein the instrument comprises a spatial light modulator (SLM).

17. The apparatus of claim 16, wherein the instrument comprises one or more projection optics for imaging the spatial light modulator onto the instrument end of the fiber.

18. The apparatus of claim 14, wherein the instrument comprises one or more light sources for illuminating the animal subject.

19. The apparatus of claim 14, wherein the instrument comprises one or more light sources for stimulating the subject.

20. The apparatus of claim 14, wherein the imaging implant comprises a gradient index (GRIN) lens.

21. The apparatus of claim 14, wherein the imaging implant comprises an imaging fiber.

22. The apparatus of claim 14, wherein the instrument comprises a rotation compensator disposed in an optical path for compensating the image rotation caused by the movement of the animal subject.

23. The apparatus of claim 22, wherein the rotation compensator comprises a Dove prism for rotating at half of the speed of the rotary joint.

24. The apparatus of claim 14, wherein the instrument comprises:
- a rotation compensator disposed in an optical path for compensating the image rotation caused by the movement of the animal subject; and
- a controller for reading the angle information from the angle encoder and controlling the rotation compensation based on the received angle information.

25. The apparatus of claim 24, wherein the rotation compensator comprises a Dove prism for rotating at half of the speed of the rotary joint.

26. The apparatus of claim 14, wherein the apparatus comprises a microendoscope.

\* \* \* \* \*